United States Patent
Shiau et al.

(10) Patent No.: US 6,780,332 B2
(45) Date of Patent: Aug. 24, 2004

(54) ANTIMICROBIAL FILTRATION

(75) Inventors: Yen-Kuen Shiau, Taipei (TW);
Chung-Hsun Wu, Tao-Yuan (TW);
Vincent T Chuang, Lin-Kou (TW)

(73) Assignee: Parker Holding Services Corp.

( * ) Notice: Subject to any disclaimer, the term of this patent is extended or adjusted under 35 U.S.C. 154(b) by 33 days.

(21) Appl. No.: 09/802,949

(22) Filed: Mar. 12, 2001

(65) Prior Publication Data

US 2001/0009239 A1 Jul. 26, 2001

Related U.S. Application Data

(60) Continuation-in-part of application No. 09/356,549, filed on Jul. 19, 1999, now Pat. No. 6,251,417, which is a division of application No. 09/046,834, filed on Mar. 25, 1998, now Pat. No. 6,051,246.

(30) Foreign Application Priority Data

Mar. 28, 1997 (TW) .................................. 86103892 A

(51) Int. Cl.[7] .................................................. C02F 1/50
(52) U.S. Cl. ........................ 210/755; 210/764; 210/501; 422/28; 422/37; 424/421; 424/619; 424/630; 514/642
(58) Field of Search .................................. 210/668, 755, 210/764, 282, 284, 290, 501; 422/28, 37; 424/421, 618, 619, 630; 514/642

(56) References Cited

U.S. PATENT DOCUMENTS

| | | | | |
|---|---|---|---|---|
| 3,618,774 A | * | 11/1971 | Delphia | 210/128 |
| 3,865,728 A | * | 2/1975 | Abbott et al. | 210/169 |
| 4,407,865 A | * | 10/1983 | Nice | 427/217 |
| 4,463,031 A | * | 7/1984 | Someya | 427/217 |
| 5,006,245 A | * | 4/1991 | Yukishita | 210/256 |
| 5,122,272 A | * | 6/1992 | Iana et al. | 210/473 |
| 5,169,625 A | * | 12/1992 | Blank | 424/65 |
| 5,432,077 A | * | 7/1995 | Farrah | 435/244 |
| 6,051,246 A | * | 4/2000 | Shiau et al. | 424/409 |
| 6,251,417 B1 | * | 6/2001 | Shiau et al. | 424/408 |
| 6,471,876 B1 | * | 10/2002 | Hansen et al. | 210/764 |

* cited by examiner

Primary Examiner—Peter A. Hruskoci
(74) Attorney, Agent, or Firm—Alice L. Chen; Chen Patents

(57) ABSTRACT

A water treating system utilizes antimicrobial sand filter for killing bacteria and preventing microbial growth. Said antimicrobial sand filter consists of organic quaternary ammonium salt and inorganic metal compound.

4 Claims, 1 Drawing Sheet

◆ - Experiment of Honeycomb w/o coating of Quaternary Ammonium Salt (performed simultaneously with ▢ ,Experiment of Honeycomb treated with Quaternary Ammonium Salt for *Legionella pneumophila*).

▢ - Experiment of Honeycomb treated with Quaternary Ammonium Salt for *Legionella pneumophila*.

▲ - Experiment of Honeycomb treated with Quaternary Ammonium salt for *Salmonella typhimurium*.

⊙ - Experiment of Honeycomb treated with Quaternary Ammonium salt for *Escherichia coli*.

ANTIMICROBIAL FILTRATION

This is a continuation-in-part of an allowed application, Ser. No. 09/356,549, filed on Jul. 19, 1999, now U.S. Pat. No. 6,251,417 which is a division of Ser. No. 09/046,834, filed on Mar. 25, 1998, now U.S. Pat. No. 6,051,246, which claims foreign priority based on a Taiwan application, 86103892, filed on Mar. 28, 1997, now abandoned.

BACKGROUND OF THE INVENTION

1. Field of the Invention

This invention relates to a novel antimicrobial filter and a filtration process employing said filter. More specifically, it relates to a water treatment process comprising filtering water through a bed of sand which is coated with antimicrobial chemicals that kill and prevent the growth of bacteria.

2. Prior Art

Antimicrobial metals have been known to be incorporated into paints and fibers for industrial or home applications. Organic quaternary ammonium silane has been shown to have anti-algae properties. The following patents show the use of silver, copper, and zinc in antimicrobial substances, and the use of organosilicon compounds.

U.S. Pat. No. 3,865,728 discloses an organosilicon compound coated on a fibrous substrate and then heated to 65–100 degrees C. The resulting product is used for control of algae in aquarium tanks.

U.S. Pat. No. 5,147,686 discloses an antimicrobial powder made by coating a titanium oxide substrate with antimicrobial metals including copper, zinc or alloys of Cu—Zn, Cu—Ag, Cu—Al, Cu—Sn or a combination of these metals. The composition is useful against various microorganisms such as E. Coli, Salmonella typhimurium, and others. The coated substrate is fired at 400 degrees C. The powder form of this product is intended to be incorporated into a resin.

U.S. Pat. No. 5,151,122 relates to an antibacterial ceramic material. Various ceramics such as zeolite or alumina or clay are described as being fired at temperatures as high as 1200–1300 degrees C. so as to lock in the absorbed antibacterial metals such as silver, copper, or zinc. The patent further suggests that the product can be added to a resin which can be molded into any shape.

U.S. Pat. No. 5,415,775 relates to an ultrafiltration membrane consisting of alumina and titanium dioxide which has been sintered at 1000–1500 degrees C. and then coated with metal oxide. The membrane exhibits anti-bacterial properties.

U.S. Pat. Nos. 5,618,762, 5,503,840, and 5,595,750 variously show Ag, Cu, Zn. Pt, Cd, Cr as antibacterial components including protective coatings.

None of the above patents addresses the problem of keeping water in reservoirs, cooling tower basins, public baths, and fish farms clear of harmful micro-organisms including algae or bacteria. In addition to its antimicrobial properties, the filter of the present invention is economical and shows high efficacy due to the small particle size structure of the sand which provides sufficient antimicrobial sites per unit volume and prolonged antimicrobial efficacy in flowing water due to strong adhesion of the antimicrobial components on the substrate, without any adverse environmental effects such as are encountered when chemical pesticides, bactericides or herbicides are used.

The object of this invention is to provide antimicrobial filters having coated thereon a metal composition such as silver or copper, or coated with an organic quaternary ammonium salt according to a specific process capable of eliminating harmful microbes such as E. coli, Salmonella typhimurium, and Saccharomycetes such as Saccharomyces cerevisiae, Candida albicans; Algae groups, such as Blue Green Algae, Brown Algae, and Green Algae, and Bacteria such as Chaetomium globosum, Penicillium funiculosum including Legionella pneumophila. Another object is to provide a process for treating water with inexpensive filter media which have been treated with the antimicrobial substances of this invention. Such filter media are easily handled and can be changed as frequently as necessary to eliminate harmful microbes. The method of filtering water can be carried out in commercially available equipment. The coated sand can be filled in a water container or encased in a container formed by a mesh screen whose mesh openings are smaller than the sand particles. The container can then be replaced when the chemical coating is spent. These objects of the invention will become apparent from the following description.

This embodiment of the invention is more economical than the honey-comb shaped substrate of applicant's above-mentioned application. The coatings of sand with silver or copper may be based on the method described in the prior application except for the elimination of calcining aids in both organic and inorganic coatings.

In this invention, the sand treated with antibacterial substances removes suspended solids and eliminates bacteria and prevents their growth in the water.

SUMMARY OF THE INVENTION

The organic antimicrobial component is a quaternary ammonium salt having the formula:

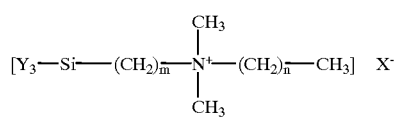

wherein m+n is 16 to 19, m is 1 to 6, and n is 13 to 17; or m+n is 20 to 23, m is 4 to 11 and n is 9 to 17 X is halogen; and Y is a hydrolyzable radical or hydroxy group. The inorganic antimicrobial components are silver or copper. These antimicrobial metal components are individually coated on sand with appropriate metals, and the coated sands are used as filter media either singly or in combination including inorganic-coated sand, to clean water.

DETAILED DESCRIPTION OF THE INVENTION

Figure 1:
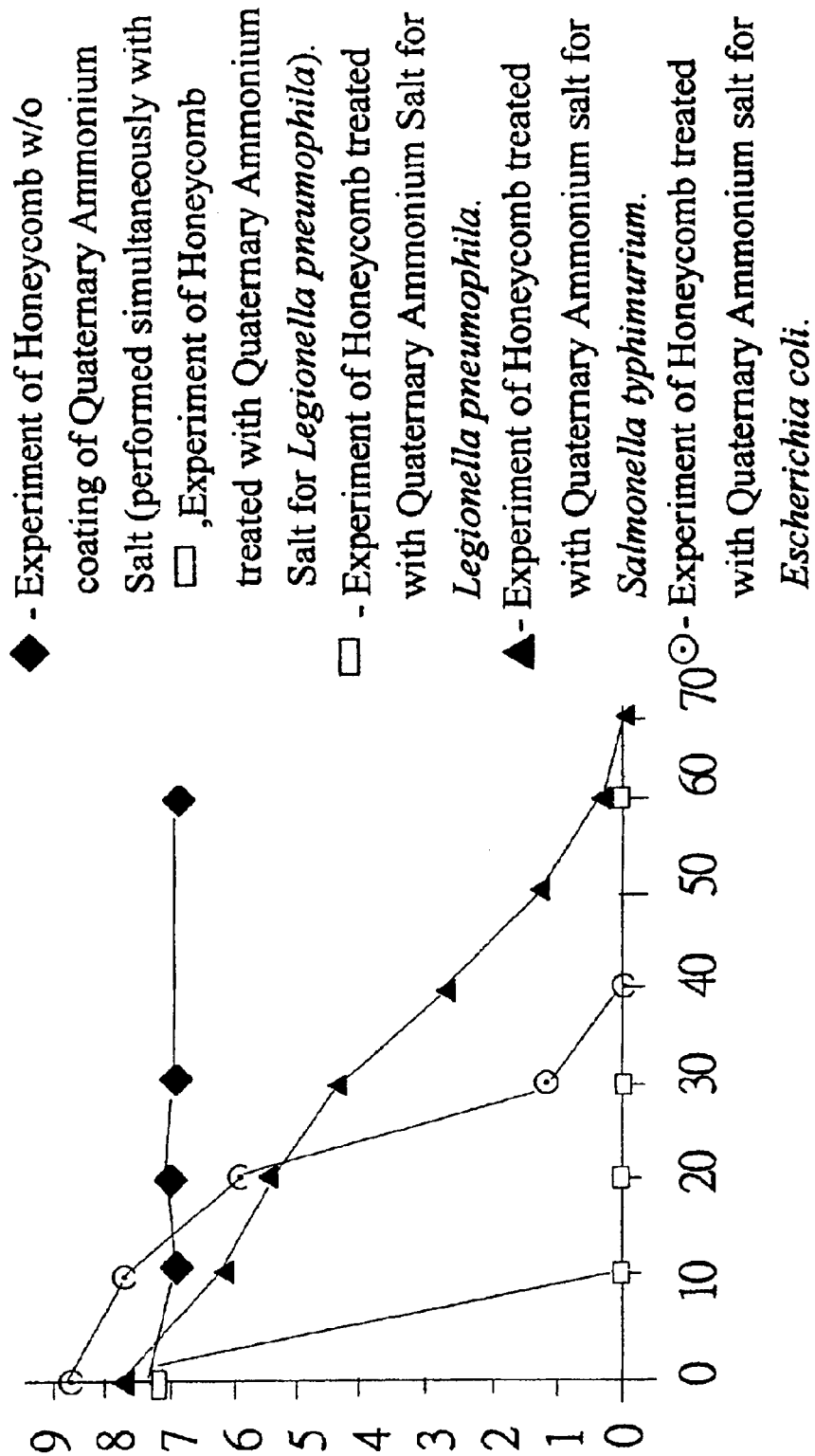
FIG. 1 shows the survival rate of the bacteria in accordance with the invention of an organic antimicrobial coating on a honeycomb-shaped substrate.

Sand having a particle size corresponding to 10–20 mesh screens is impregnated with 1% by weight of silver nitrate solution, or 1% by weight of copper nitrate solution, respectively. The coated sand at is then calcined at 500 degrees C. for about 4 hours. The calcined coated sand is then washed in an ultrasonic cleaner to ensure that no loose chemicals adhere to the sand particles.

The coating processes for the quaternary ammonium salts are described below. In addition, the organically coated sand is tested with bromophenol blue to ensure the coated sand is quantitatively indicating the presence of quaternary ammonium salt. A blue color indicates that the ammonium salt is at full strength. This is a reliable and convenient quality control method.

Quaternary ammonium orgnanosiloxane salt (herein referred to as quaternary ammonium salt) used as algicide by coating on a fibrous material as shown in U.S. Pat. Nos. 3,817,452 and 3,865,728 forms no part of this invention. Rather, this invention provides a new method of preparing an antimicrobial filter. Moreover, the filter kills not only algae but also bacteria.

In the process of coating the sand, the quaternary ammonium salt is dissolved in water to form a moiety of —Si(OH)$_3$ and the sand is soaked in the solution. The moiety of the quaternary ammonium salt reacts with the sand, $SiO_2$, thereby forming a strong bond. 3-(Trimethoxysilyl)-propyidimethyloctadecyl ammonium chloride is representative of the group of silyl quaternary ammonium salts that may be used in the instant application.

It has been found that in the process of making the organic antimicrobial filter of this invention, a special calcining aid may be used to enhance the adhesion or bonding of the quaternary ammonium salt to the substrate. The calcining aid is aluminum oxide with high pore surface per unit volume, such as Boehmite, which is available from Condea Corporation in Germany. Other calcining aids can be $SiO_2$ or $SiO_2Al_2O_3$.

In the preparation of the organic antimicrobial filter, aluminum oxide may be mixed with water in the ratio of 1:1 to 1:10 by weight. An acid such as nitric, hydrochloric, or oxalic acid is added to adjust the pH to 3–6. After the mixture is ground to a gelatinous solution, the sand is immersed in the gelatinous solution. This calcining-aid-coated sand is then calcined at 400 to 1500° C., preferably at 500 to 800° C.

Quaternary ammonium salt is dissolved in a solvent selected from the group consisting of water, alcohols, ketones, esters, hydrocarbons, and chlorinated hydrocarbons in a concentration of about 0.05 to 20%, preferably 0.3 to 0.6% by weight. Water is the preferred solvent. The calcined sand prepared as described above is impregnated with the quaternary ammonium salt solution until it is saturated or until 50% of the solution is absorbed. The impregnated sand is then dried at 50 to 200° C., preferably at 60 to 150° C. to form the organic antimicrobial filter. Drying time depends on the amount of sand used. In a simplified process, the sand is directly placed in the 0.3 wt % of quaternary ammonium salt to saturate the sand and then dried at about 150° C.

The antimicrobial filter of this invention may be placed in circulating water such as cooling tower water, to kill microbes. They may be placed in circulating air in air conditioning systems to sterilize the air. After a period of use, the filter may be regenerated by flushing with clean water or vibrated with a ultrasonic device and using a blower to remove any accumulated debris and cleaned by reversing the flow of water.

The following examples illustrate the preparation of the antimicrobial articles of this invention and their efficacy.

EXAMPLE 1

Preparation of the Inorganic Antimicrobial Filter

Prepare a solution of 1 part by weight of the metal composition Ag NO3 and 99 parts by weight water. 10 mesh sand is added to the solution to be impregnated till saturation. Excess solution is drained. The coated substrate is calcined at 800–900° C.

Prepare a solution of 1 parts by weight of the metal composition Cu(NO3)2.3H$_2$O and 99 parts by weight water. 10 mesh sand is added to the solution to be impregnated till saturation. Excess solution is drained. The coated substrate is calcined at 800–900° C.

Process of Producing Organic Antimicrobial Filter

Into 100 ml. of 0.3 wt. % aqueous solution of 3-(trimethoxysilyl)propyldimthyloctadecyl ammonium chloride, there is dipped 100 grams of sand substrate to soak until saturated. At least 50% of the solution should be absorbed. The soaked substrate is dried at 100° C. for about 30 minutes to allow chemical bonding to occur.

The inorganic coated sand may be mixed with the organic coated sand. Also the water flow may be reversed, with the water coming from bottom of the water tank, passing upward through the coated sand filter and leaving the water tank from the top. The reversed flow is intended to increase the contact with the filter and create more turbulent flow.

Any tank fitted with inlet and outlet pipes may be used to implement the cleaning process of this invention. Provisions should be made to facilitate the change of antimicrobial sand. Alternatively, the antimicrobial sand may be enclosed in a wire mesh case whose mesh openings are smaller than the sand particles.

It has been established in U.S. Pat. No. 6,051,246, this applicants' prior invention, the efficacy of the quaternary ammonium salt coated on a honey-comb shaped substrate as follows:

Example 7 in its entirety of U.S. Pat. No. 6,051,248 is incorporated by reference. FIG. 1 shows the survival rate of each type of bacteria. *Legionelia pneumophila* dies within 10 minutes in contact with the antimicrobial article. *E. coli* dies after 40 minutes and *Salmonella typhimurium* after about 60 minutes. The control show the same rate of survival of *Legionelia pneumophila* as first inoculated. The efficacy of quaternary ammonium salt on sand should have the same effect. Following are the test for the efficacy of the coated sand filter.

EXAMPLE 2

Test for Efficacy of Antimicrobial Filters

Four samples of sand, each containing 5 g: sand without coating (Control); sand coated with quaternary ammonium salt (A); sand coated with copper compound (B) and sand coated with silver compound (C). All the coating is done according the above described processes. followed by washing with water to remove any loose chemical adhering on the surface. *E. coli* culture was incubated over night and diluted 100 times with nutrient. The diluted *E. coli* is evenly distributed into four 20-ml tubes. Add the four samples respectively into each correspondingly marked tube and Incubate at 37 degree C. with shaker for sufficient time to allow the bacteria to grow.

Each tube is inserted into a spectrophotometer to study the growth rate of *E. coli* and expressed as O.D (A600)., optical density.

| sample | control | A | B | C |
|---|---|---|---|---|
| O.D. | 1.46 | 0.44 | 0.91 | 0.32 |

In conclusion, the filtration process using the antimicrobial filter improves the quality of water many folds. It indicates the filter with the silver compound is the most effective antimicrobial filter.

We claim:

1. A process for treating contaminated water comprising:

filling a water tank with a predetermined amount of antimicrobial sand said sand being prepared by mixing aluminum oxide with water, adding acid to form a gelatinous solution, immersing sand in the gelatinous solution, calcining the sand at 400 to 1500 degree C., and impregnating the calcined sand with a quaternary ammonium salt solution of 3-(trimethoxysilyl)-propyldimethyloctadecyl ammonium chloride and passing said contaminated water through the antimicrobial sand which acts as a filter, to provide clean water in said tank.

2. The process of claim 1 further comprising:

introducing water to be treated through an inlet to the tank;

passing water downwardly through said sand and providing clean water at an outlet of the tank.

3. The process of claim 2, wherein water to be treated is introduced to the outlet, passing upwardly through the filter and providing clean water at the inlet.

4. The process of claim 1, wherein the antimicrobial sand is encased in a wire mesh case having mesh openings smaller than the size of the sand particles.

* * * * *